US008545392B2

(12) United States Patent
Standfest et al.

(10) Patent No.: US 8,545,392 B2
(45) Date of Patent: Oct. 1, 2013

(54) SEXUAL STIMULATION DEVICE

(76) Inventors: Christine Florence Standfest, Mancelona, MI (US); Christopher Bruce Standfest, Mancelona, MI (US)

( * ) Notice: Subject to any disclaimer, the term of this patent is extended or adjusted under 35 U.S.C. 154(b) by 778 days.

(21) Appl. No.: 12/716,869

(22) Filed: Mar. 3, 2010

(65) Prior Publication Data

US 2010/0268021 A1 Oct. 21, 2010

Related U.S. Application Data

(60) Provisional application No. 61/214,053, filed on Apr. 20, 2009.

(51) Int. Cl.
*A61F 5/00* (2006.01)

(52) U.S. Cl.
USPC .......... 600/38

(58) Field of Classification Search
USPC .......... 600/38–41; 601/46, 72, 107, 110, 601/112
See application file for complete search history.

(56) References Cited

U.S. PATENT DOCUMENTS

2006/0041310 A1* 2/2006 Williams .......... 623/15.12
2009/0171144 A1* 7/2009 Squicciarini .......... 600/38

* cited by examiner

*Primary Examiner* — Samuel Gilbert

(74) *Attorney, Agent, or Firm* — Vincent G. LoTempio; Kloss, Stenger & LoTempio; David T. Stephenson

(57) ABSTRACT

A sexual stimulation device which provides simultaneous stimulation to male and female partners during intercourse includes a hollow elastomeric shaft portion dimensioned to receive a penis and for vaginal insertion. The shaft includes a longitudinal rib forming an interior channel, the rib functioning to stiffen the shaft and the channel providing sufficient resilience to allow insertion and removal of a penis. The shaft terminates at a closed end in a hemispherical tip and at an opposite open end in a pair of spaced annular retaining rings. A plurality of raised rings spaced axially along the shaft enhance the pleasure of the female partner. The retaining rings provide a resilient retaining force to maintain the device in position during intercourse. An electric motor with an eccentric weighted flywheel mounted in a chamber extending between the annular rings provides vibratory stimulation. An electrical wire for powering the vibratory motor extends through a conduit connecting the chamber to an attached housing enclosing rechargeable batteries. The housing also includes a second motor operably connected for rotating caged massage balls positioned to provide simultaneous stimulation to a female partner during intercourse. An elastomeric shell encloses and substantially seals the housing, while still allowing user actuation of two HIGH-LO-OFF switches providing independent control of the two motors and connection of an AC adapter for recharging the batteries. In an alternative embodiment, the hollow shaft may be omitted.

16 Claims, 13 Drawing Sheets

SEXUAL STIMULATION DEVICE

CROSS-REFERENCE TO RELATED APPLICATIONS

This application is a nonprovisional utility patent application which hereby references and claims the priority of Provisional Application No. 61/214,053 filed Apr. 20, 2009 and entitled Simultaneous Duel Stimulation Device For Men And Women Includes Option Of Protected Contraceptive Uses As Well Is To Be Worn While Sexual Activity Takes Place.

BACKGROUND OF THE INVENTION

1. Field of the Invention

The application relates to the field of sexual stimulation devices.

2. Description of the Related Technology

U.S. Pat. No. 3,996,930 which issued to M. Sekulich on Dec. 14, 1976, disclosed a self-contained gynecologic stimulator formed by a resilient V-shaped member.

U.S. Pat. No. 4,574,791 which issued to M. Mitchener on Mar. 11, 1986 discloses a muscle-toning device including a vaginal insert member connected by a flexible or stretchable cable to an exteriorly disposed support body.

U.S. Pat. No. 5,690,603 which issued to M. Kain on Nov. 25, 1997 discloses an erogenic stimulator designed to provide simultaneous stimulation to a couple.

U.S. Pat. No. 5,853,362 which issued to D. Jacobs on Dec. 29, 1998 discloses a stimulator device adapted for intravaginal insertion.

U.S. Pat. No. 6,053,881 which issued to A. Boodramsingh et al. on Apr. 25, 2000 discloses an ankle massaging device constructed in the shape of a "U" with each end provided with an internal battery powered vibratory electric motor to provide a massage to opposite sides of a users ankle.

U.S. Pat. No. 6,190,307 which issued to C. Tsai on Feb. 20, 2001 discloses an erotic implement adapted for vaginal insertion and including a vibrator and a massage unit consisting of battery powered rotating beads.

U.S. Pat. No. 7,341,566 which issued to S. Nan on Mar. 11, 2008 discloses a massage apparatus having a battery powered massage device controlled by a remote control panel connected by a wire.

U.S. Patent Application Publication No. 2004/0230093 published Nov. 18, 2004 discloses a stimulation aid comprising a U-shaped implement which may be vibrated or pulsed by an imbedded electric motor.

U.S. Patent Application Publication No. 2008/0009775 published Jan. 10, 2008 discloses an electro-mechanical sexual stimulation device having a pair of internal battery powered motors.

U.S. Patent Application Publication No. 2008/0221387 published Sep. 11, 2008 discloses a vibrating toothbrush attachment for use as a sexual aid or for muscular stimulation. The device includes an oscillating tip member having knob-like protrustions.

U.S. Design patent No. D517,217 which issued to J Zou et al. on Mar. 14, 2006 discloses an ornamental design for a generally U-shaped Wand Massager.

The entire disclosure of each of the aforementioned patents and published patent applications is incorporated herein by this reference thereto.

SUMMARY OF THE INVENTION

A sexual stimulation device which provides simultaneous stimulation to male and female partners during intercourse includes a hollow elastomeric shaft portion dimensioned to receive a penis and for vaginal insertion. The shaft includes a longitudinal rib forming an interior channel, the rib functioning to stiffen the shaft and the channel providing sufficient resilience to allow insertion and removal of a penis. The shaft terminates at a closed end in a hemispherical tip and at an opposite open end in a pair of spaced annular retaining rings. A plurality of raised rings spaced axially along the shaft enhances the pleasure of the female partner. The retaining rings provide a resilient retaining force to maintain the device in position during intercourse. An electric motor with an eccentric weighted flywheel mounted in a chamber extending between the annular rings provides vibratory stimulation. An electrical wire for powering the vibratory motor extends through a conduit connecting the chamber to an attached housing enclosing rechargeable batteries. The housing also includes a second motor operably connected for rotating caged massage balls positioned to provide simultaneous stimulation to a female partner during intercourse. An elastomeric shell encloses and substantially seals the housing, while still allowing user actuation of two HIGH-LO-OFF switches providing independent control of the two motors and connection of an AC adapter for recharging the batteries. In an alternative embodiment, the hollow shaft may be omitted.

These and various other advantages and features of novelty that characterize the invention are pointed out with particularity in the claims annexed hereto and forming a part hereof. However, for a better understanding of the invention, its advantages, and the objects obtained by its use, reference should be made to the drawings which form a further part hereof, and to the accompanying descriptive matter, in which there is illustrated and described a preferred embodiment of the invention.

DETAILED DESCRIPTION OF THE PREFERRED EMBODIMENT(S)

Figure 1:
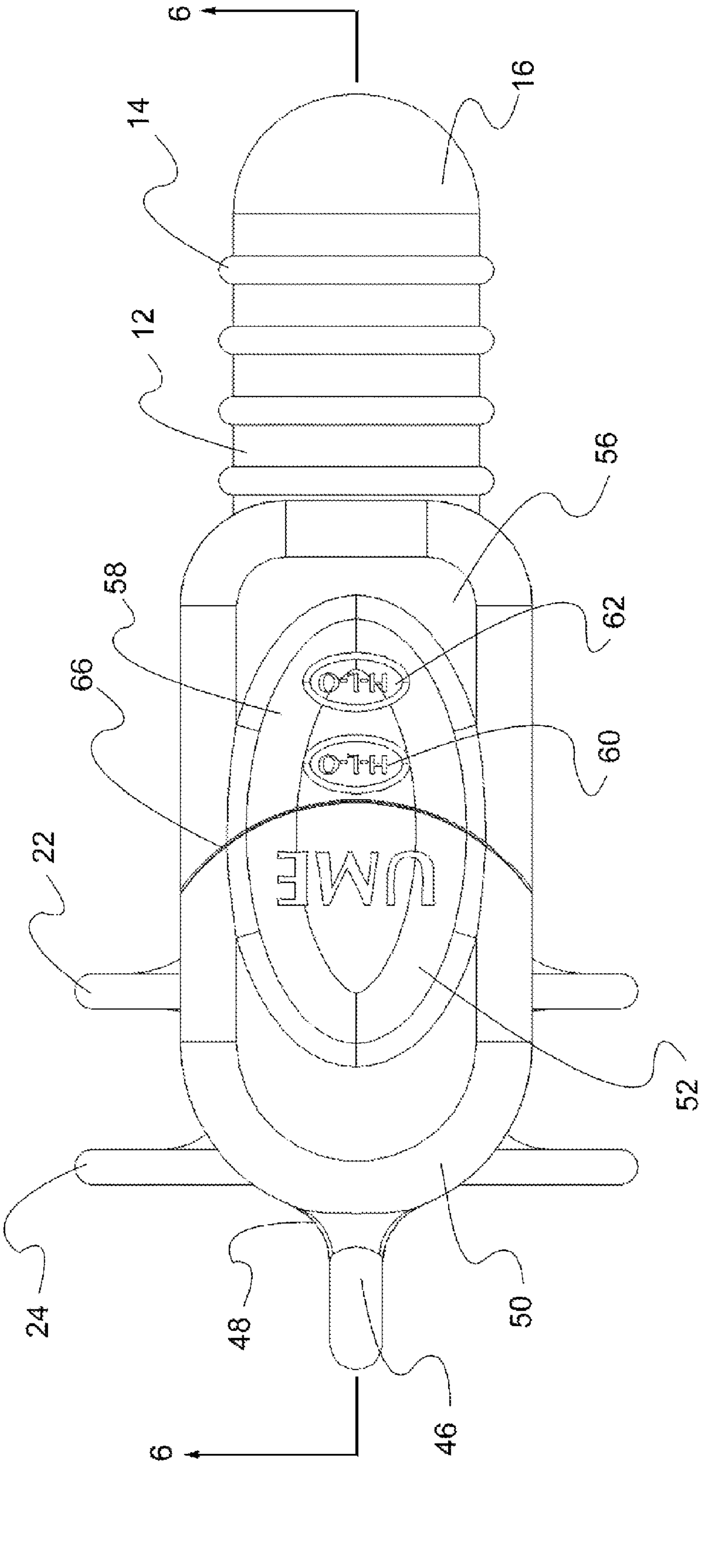
FIG. 1 is a top plan view of a sexual stimulation device according to a first preferred embodiment of the present invention.
Figure 2:
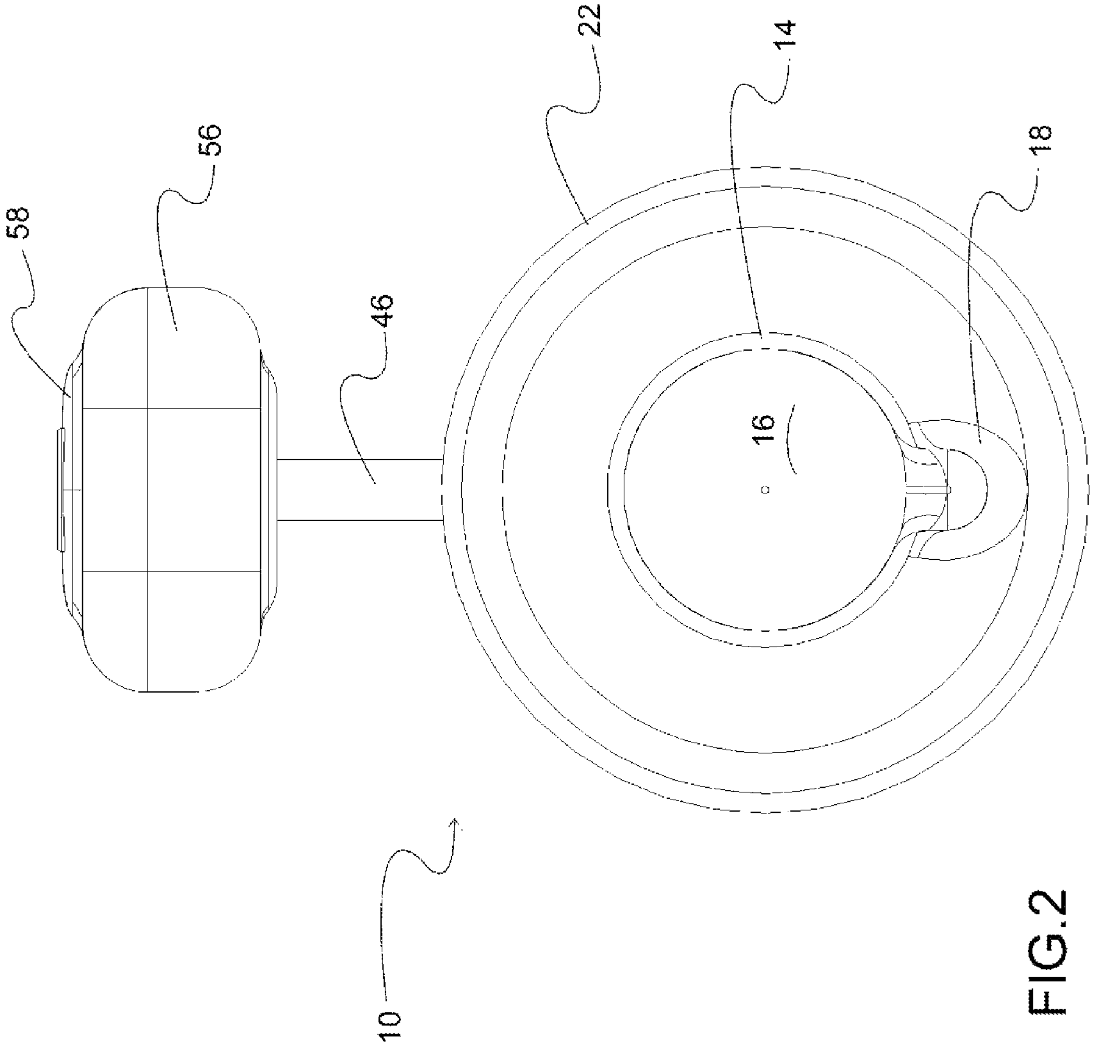
FIG. 2 is a rear elevational view of the device of FIG. 1.
Figure 3:
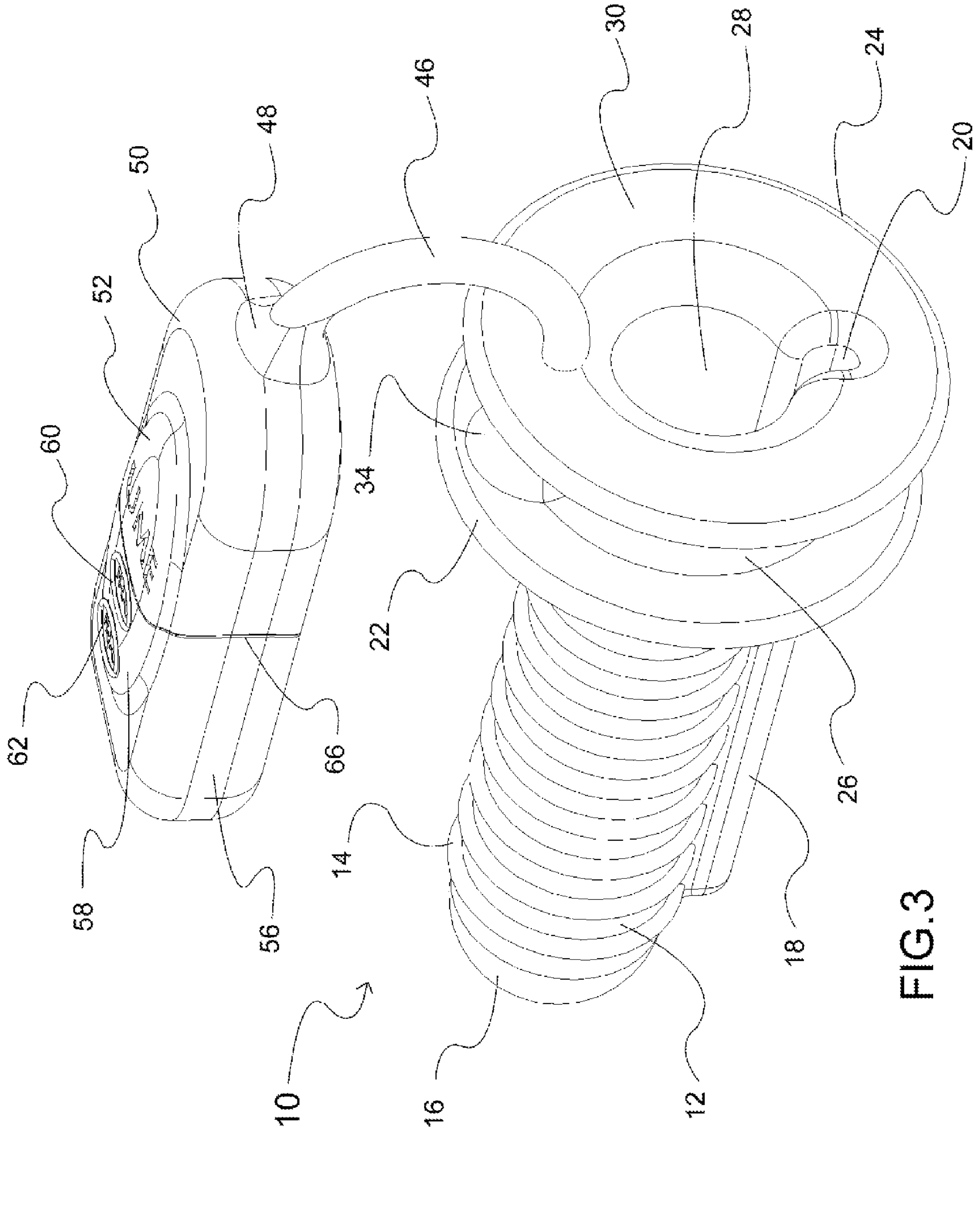
FIG. 3 is a front perspective view of the device of FIG. 1.
Figure 4:
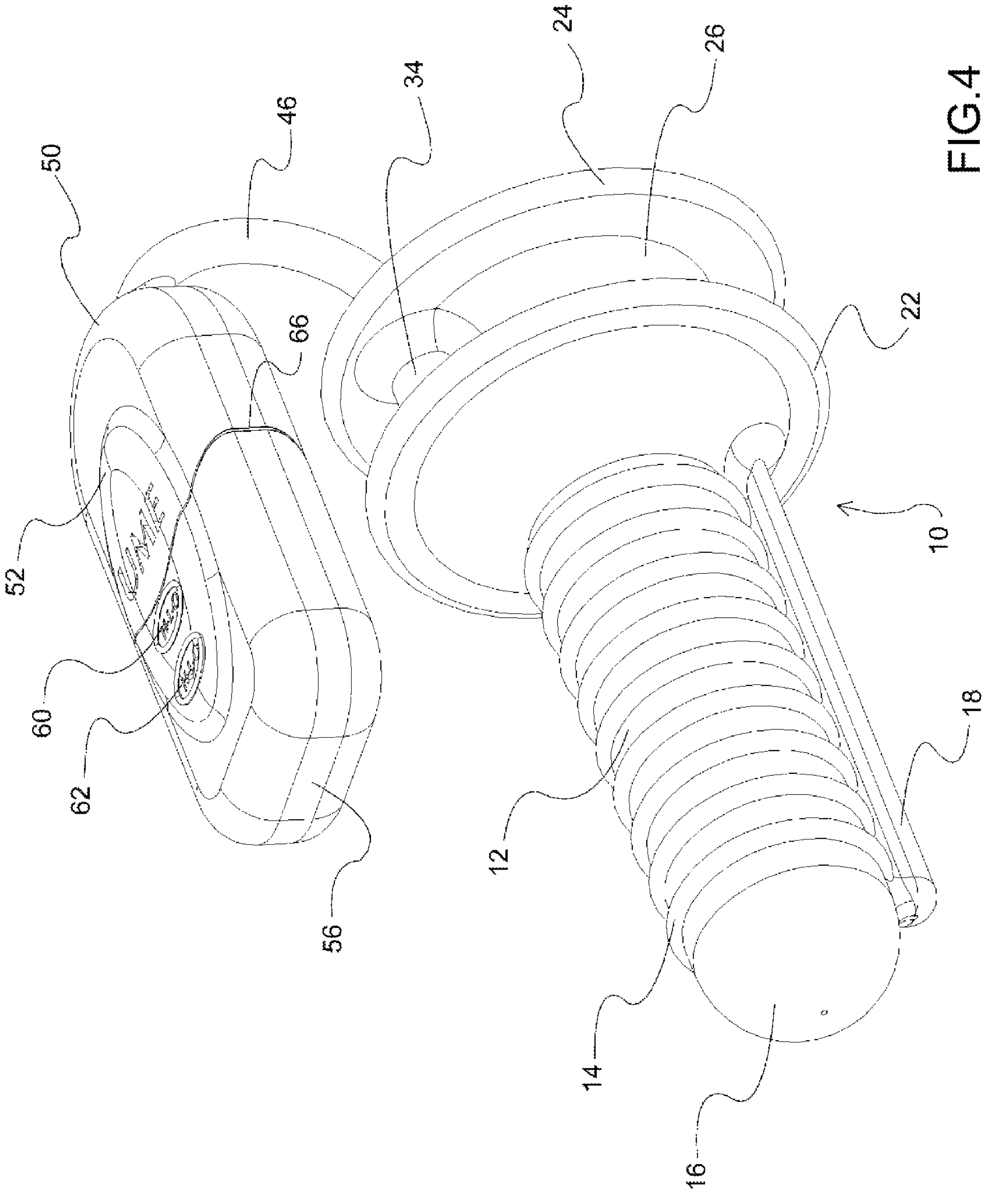
FIG. 4 is a rear perspective view of the device of FIG. 1.
Figure 5:
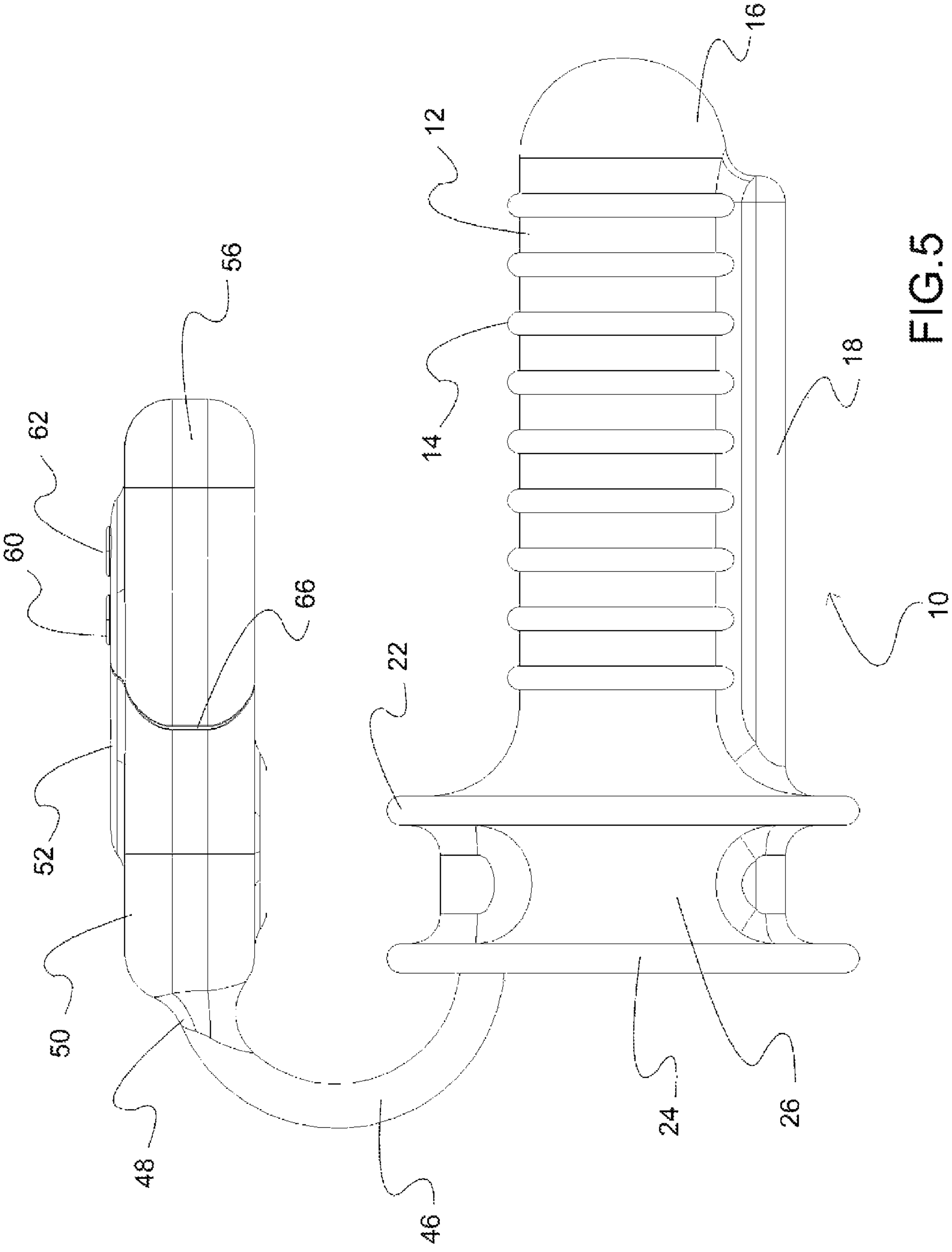
FIG. 5 is a side elevational view of the device of FIG. 1.

With reference to the drawings, and in particular to FIGS. 1 through 10, a sexual stimulation device 10 according to a first preferred embodiment of the invention will now be described. The device 10 includes a generally cylindrical hollow shaft 12 preferably formed from a silicone material and having a plurality of raised circular ridges 14 spaced evenly along a longitudinal axis of the shaft 12. The shaft 12 terminates at a distal end portion in a hemispherical tip portion 16. An elongated rib 18 extends axially along a bottom portion of the shaft 12 forming an interior channel 20 within the shaft 12. The rib 18 functions to stiffen the shaft 12, while the channel affords sufficient flexibility to allow insertion and removal of a penis. An opposite end of the shaft 12 terminates in a pair of axially spaced radially enlarged annular retaining rings 22 and 24 connected by a reduced diameter cylindrical portion 26. The retaining rings, by virtue of the channel 20, provide a resilient frictional engagement of the device with a penis sufficient to maintain the device in position during intercourse. A central circular aperture in an annular end face 30 communicates with the generally cylindrical hollow interior 28 of the shaft 12.

A hole 32 formed in the annular end face 30 communicates with a cylindrical chamber 34 extending transversely between the retaining rings 22 and 24 and having a vibration producing element 36 disposed therein. The vibration producing element 36 is encapsulated within a mating first capsule shell 38 and a second capsule shell 40. In a preferred embodiment of the invention, the vibration producing element 36 consists of a small electric motor having an eccentric flywheel 37 mounted for rotation on an output shaft of the motor. An electrical cable or wire 42 connected to the vibration producing element 36 extends through a conduit 46 and into the tubular sheath 44 surrounding the encapsulated vibration producing element 36 and received within the chamber 34. The sheath 44 is preferably formed from an elastomeric material which allows sufficient compression for insertion in close conforming engagement within the chamber 34. An opposite end of the conduit 46 terminates in a reinforced grommet region 48 merging smoothly with a first elastic skin portion 50. The first elastic skin portion 50 includes an upwardly projecting raised region 52 and a first seal portion 54 (see FIG. 7) configured for mating engagement with a second seal portion 64 of a second elastic skin portion 56. The second elastic skin portion 56 includes an upwardly projecting raised region 58 including a first switch dimple 60 and a second switch dimple 62. The elastic skin portions are preferably formed from a silicone material with a durometer of Shore A 60 in the range of 0.0625 inch to 0.25 inch thick with a durometer of The conduit 46 is preferably formed from a more rigid material such as a Shore A20 durometer silicone material.

The first skin portion 50 and second skin portion 56 mate in close conforming sealed relationship along an arcuate junction 66 and function to provide an enclosure for a housing formed by mating first 68 and second 70 housing shell portions. The housing shell portions 68 and 70 are formed with respective peripherally extending shoulders 72 and 74 such that the shell portions 68 and 70 snap together in a close conforming juxtaposed relationship. A first arcuate notch 76 formed at one end of the shell portion 68 receives the electrical wire 42 there through and a second arcuate notch at an opposite end of the shell portion 68 forms a charging port 78 adapted to receive a DC output plug of a conventional AC adapter (not shown) for the purpose of recharging a pair of batteries 80 and 82.

Figure 10:
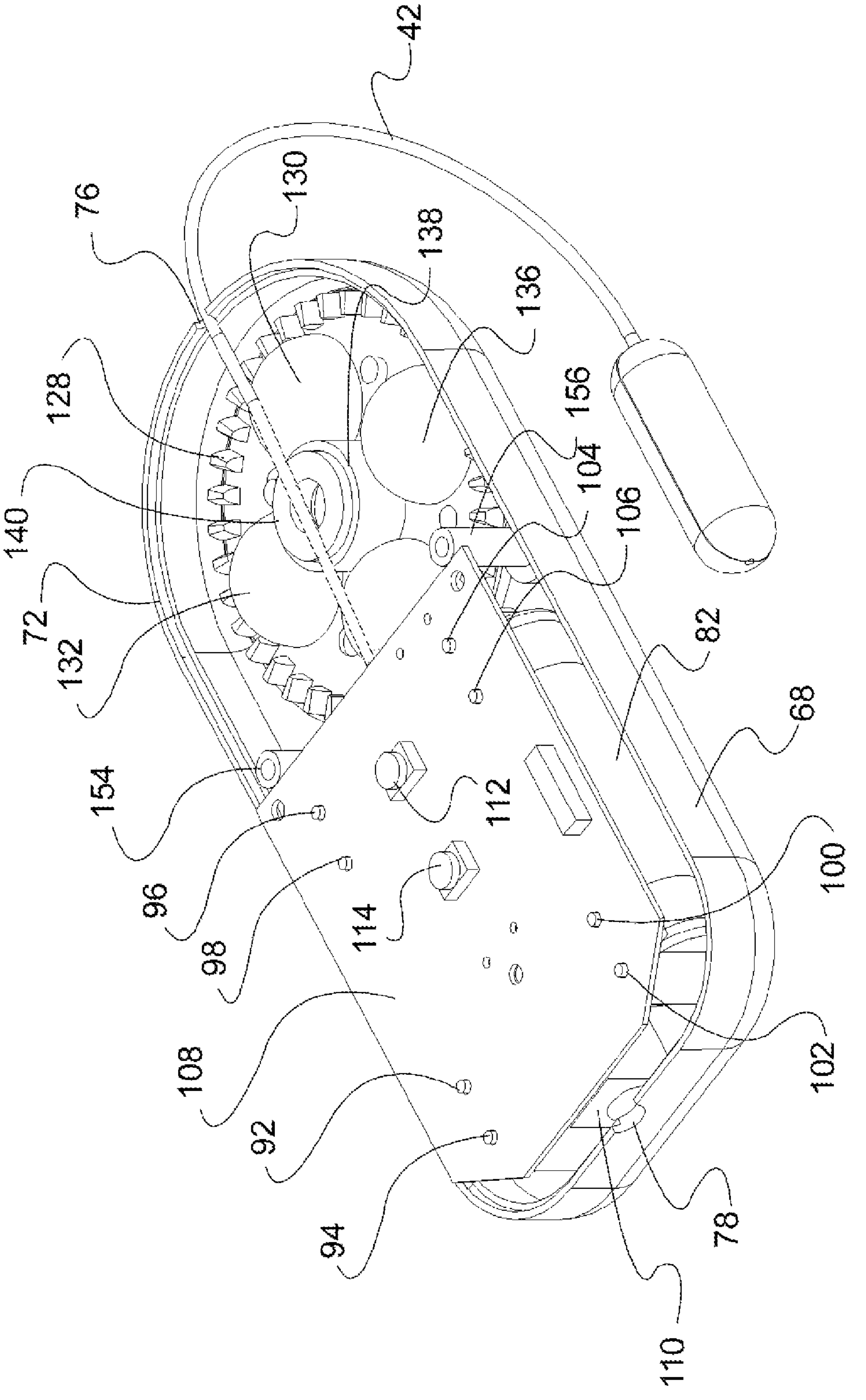
FIG. 10 is a further perspective view of the interior of the housing of FIG. 8.

Spaced battery brackets 84, 86, 88, and 90 secure the batteries 80 and 82 within the housing and include respective pairs of pins 92-94, 96-98, 100-102, and 104-106 which extend through a plurality of cooperating apertures provided through a circuit board 108, as shown in FIG. 10. A jack 110 connected to the circuit board 108 engages the DC output plug of a conventional AC adapter for charging the batteries 80 and 82.

A first three position, HI-LO-OFF micro switch 112 includes a button portion disposed in alignment with the switch dimple 60. To operate the switch, a user pushes their finger into the dimple 60 in the cover 56, which causes a leaf spring flap 116 to be deformed inwardly, actuating the switch 112. When a user releases the pressure of their finger, the spring flap 116 springs back upwardly, out of engagement with the switch. In a similar manner a second three position HI-LO-OFF micro switch 114 cooperates with the switch dimple 62 and a second leaf spring flap 118

Figure 6:
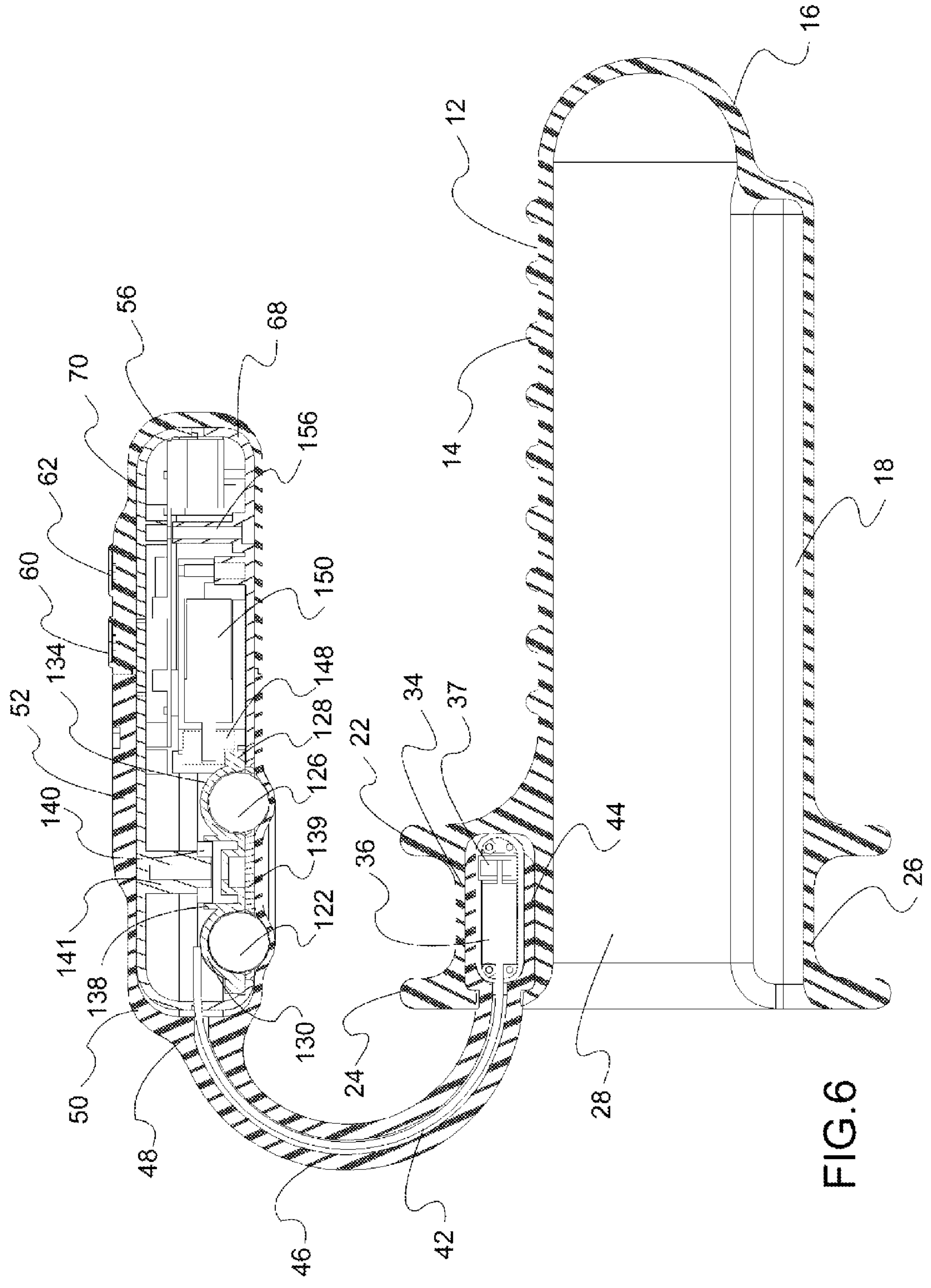
FIG. 6 is a longitudinal cross sectional view taken along line 6-6 of FIG. 1.
Figure 7:
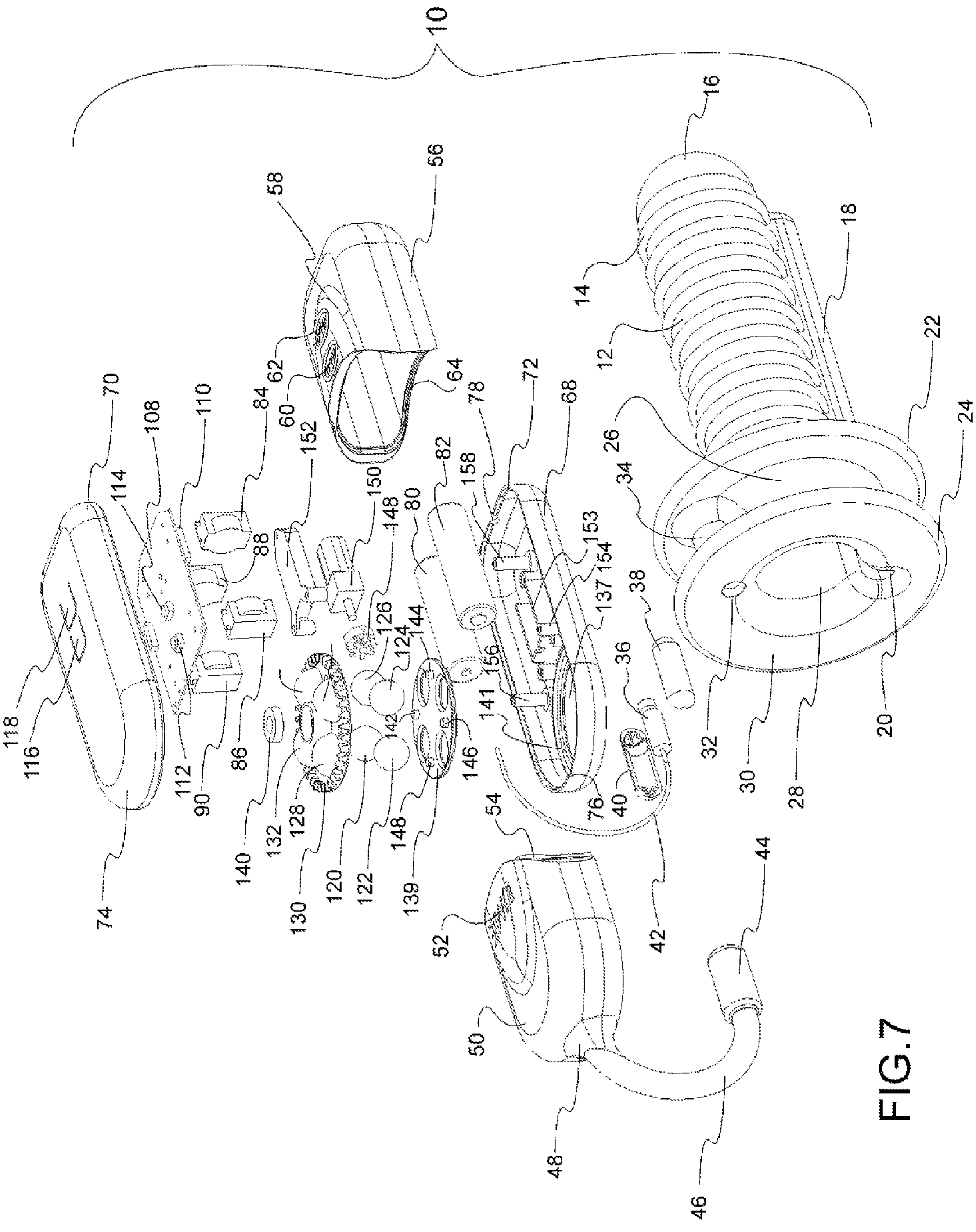
FIG. 7 is an exploded perspective view of the device of FIG. 1.
Figure 8:
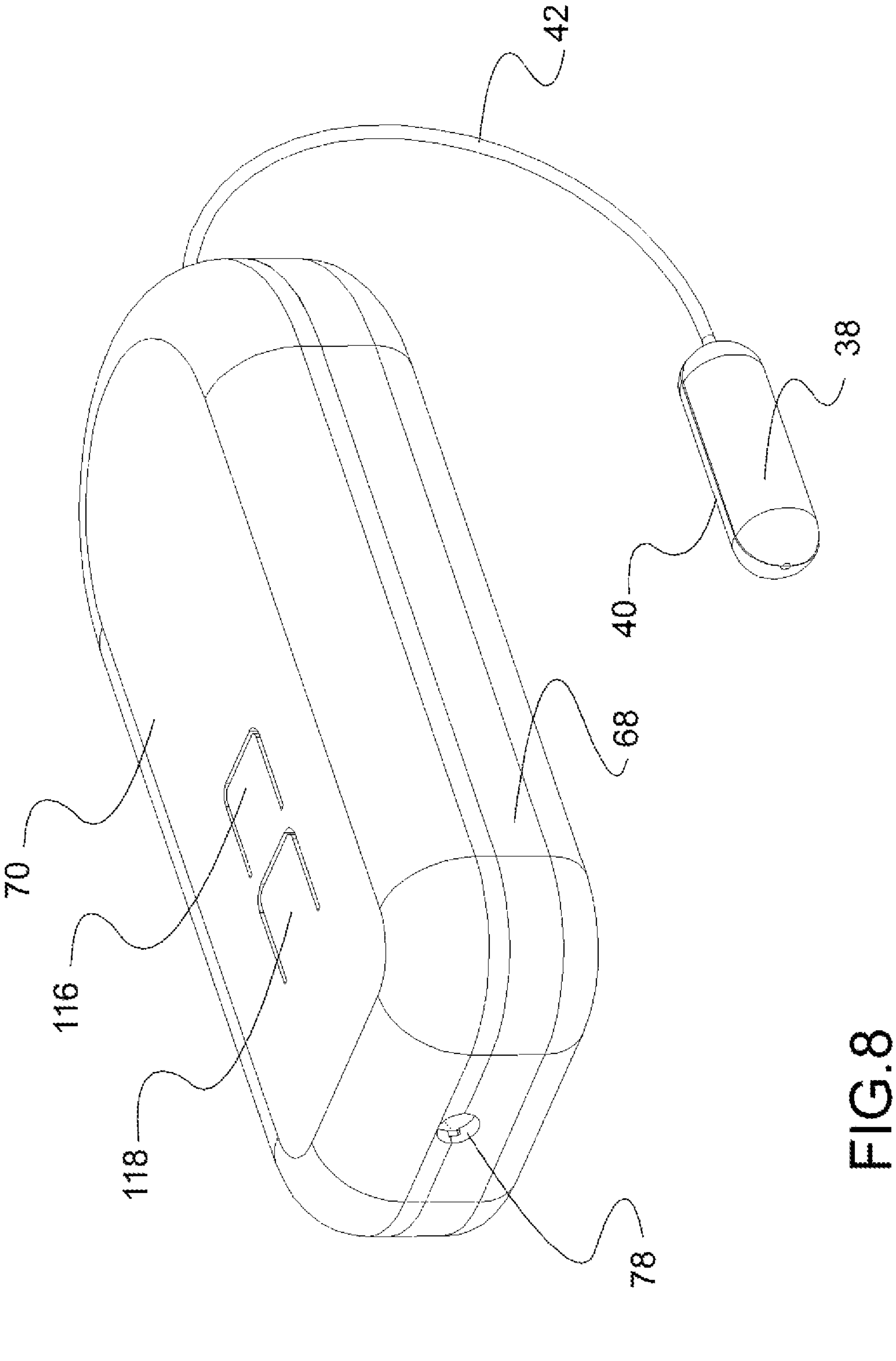
FIG. 8 is a perspective view of a housing portion of the device of FIG. 1.
Figure 9:
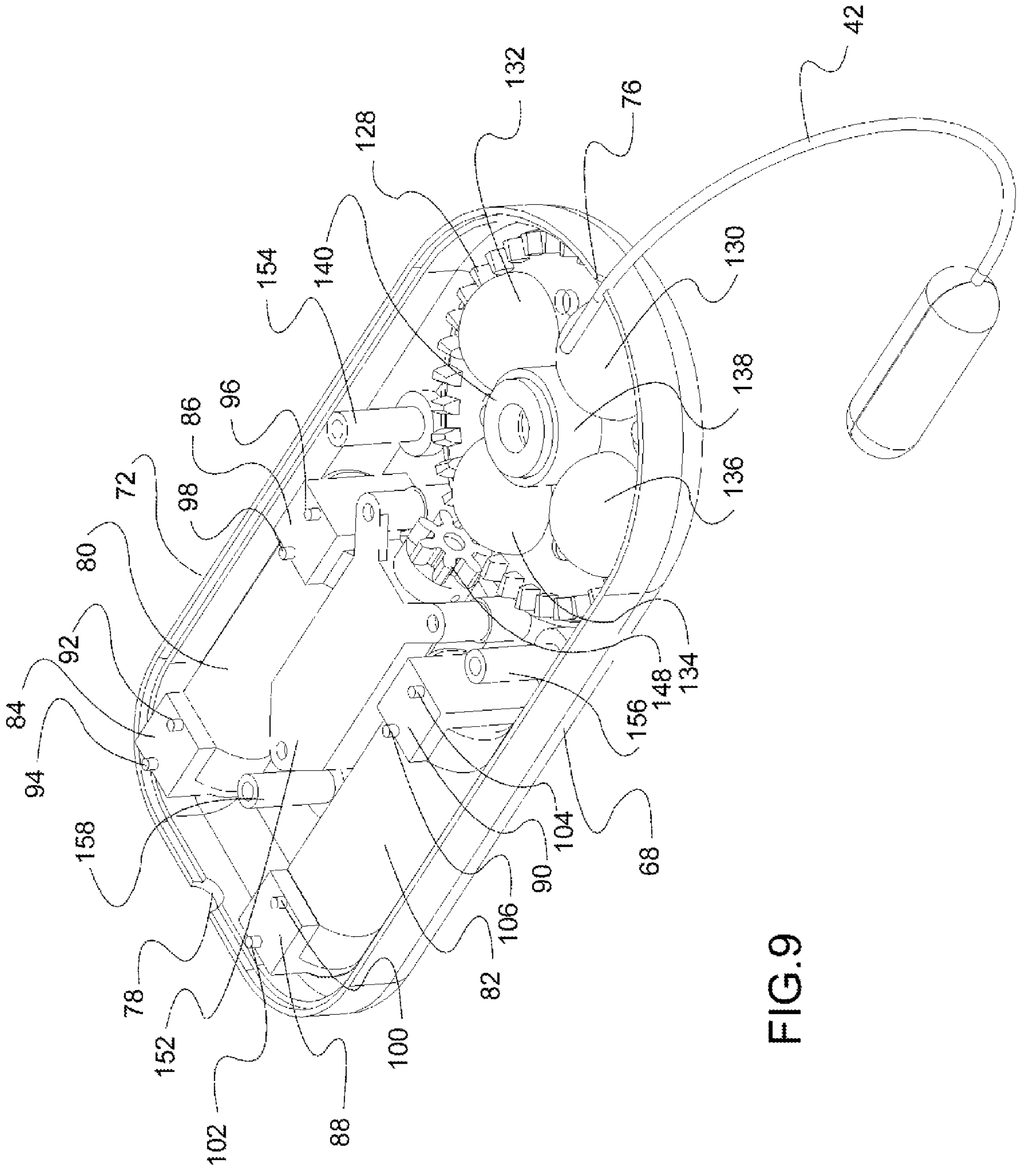
FIG. 9 is a perspective view of the interior of the housing of FIG. 8.

The sexual stimulation device 10 includes a mechanism disposed within the housing for providing massage stimulation using rotating balls 120, 122, 124, 126 constrained for rotation within ball cups 130, 132, 134, and 136 formed on a ring gear 128. The ring gear 128 includes a sleeve 138 which receives a bearing 140 which mounts the ring gear 128 for rotation about an axle 141 extending downwardly from housing shell 70, as shown in FIG. 6. A ball retaining plate 139 has four circumferentially spaced holes dimensioned to allow only partial passage of the balls there through. The retaining plate 139 includes upwardly projecting pins 140, 142, 144, and 146 which engage complementary apertures formed in the ring gear 128, such that when assembled, the balls are captured for rotation within the ball cups. A circular hole 137 is formed in the floor of the housing shell 68 exposing bottom portions of the balls into contact with a bottom portion of the elastic skin 50. An annular ledge or shoulder 141 engages a peripheral edge portion of the retaining plate 139, maintaining the plate 139 inside the housing shell 68. Positioning of the rotating massage balls in spaced relation to the shaft 12 in the orientation shown in FIG. 6 affords stimulation to the female partner during intercourse. A pinion gear 148 driven by a motor 150 drives the ring gear 128 and captures balls 120, 122, 124, and 126 in rotation. A bracket 152 secures the motor in position within the housing. Support posts 154, 156, 158 receive channel screws and serve to secure the housing shells 68 and 70 together.

Figure 11:
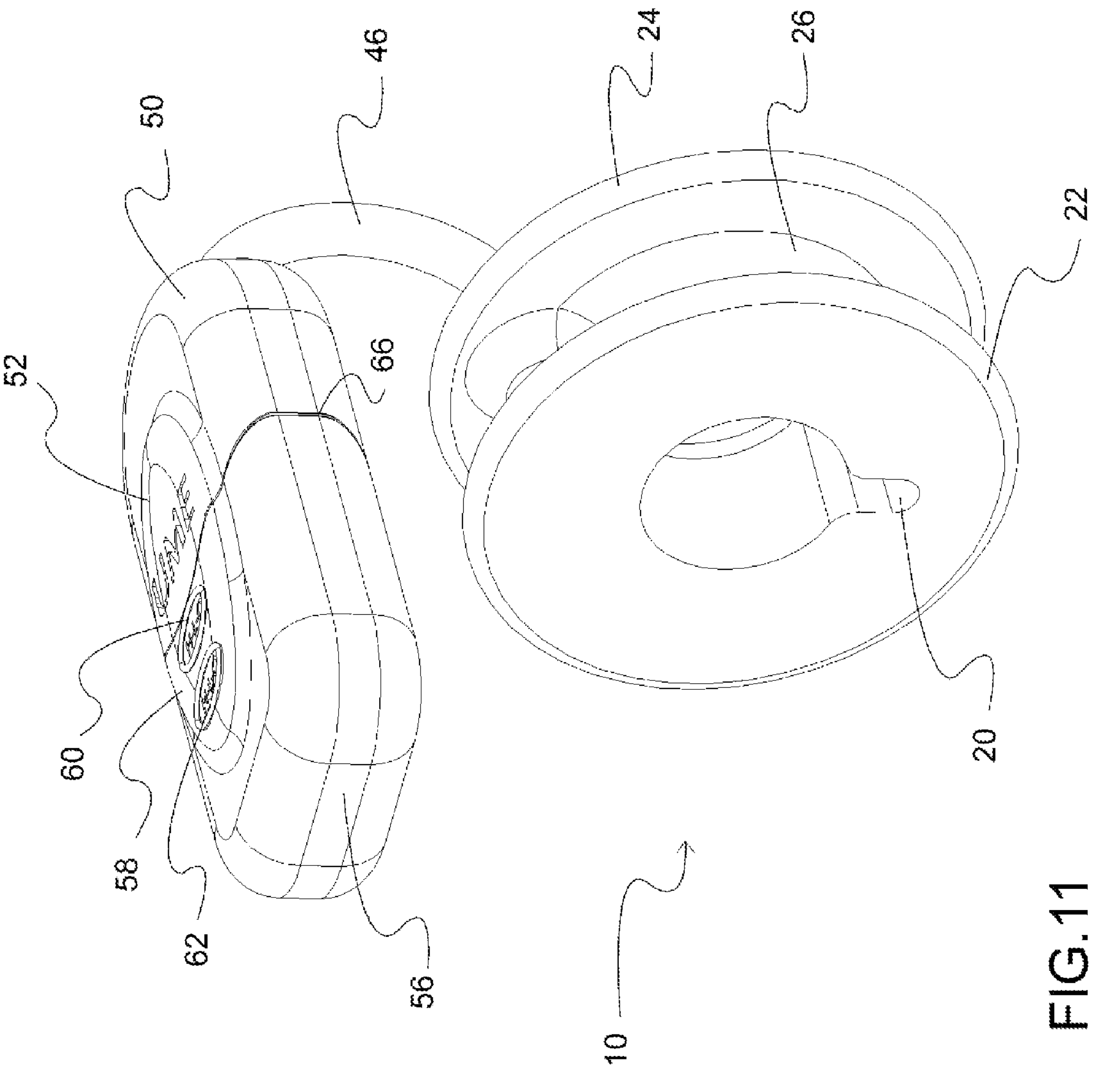
FIG. 11 is a front perspective view of a sexual stimulation device according to an alternative preferred embodiment of the present invention.
Figure 12:
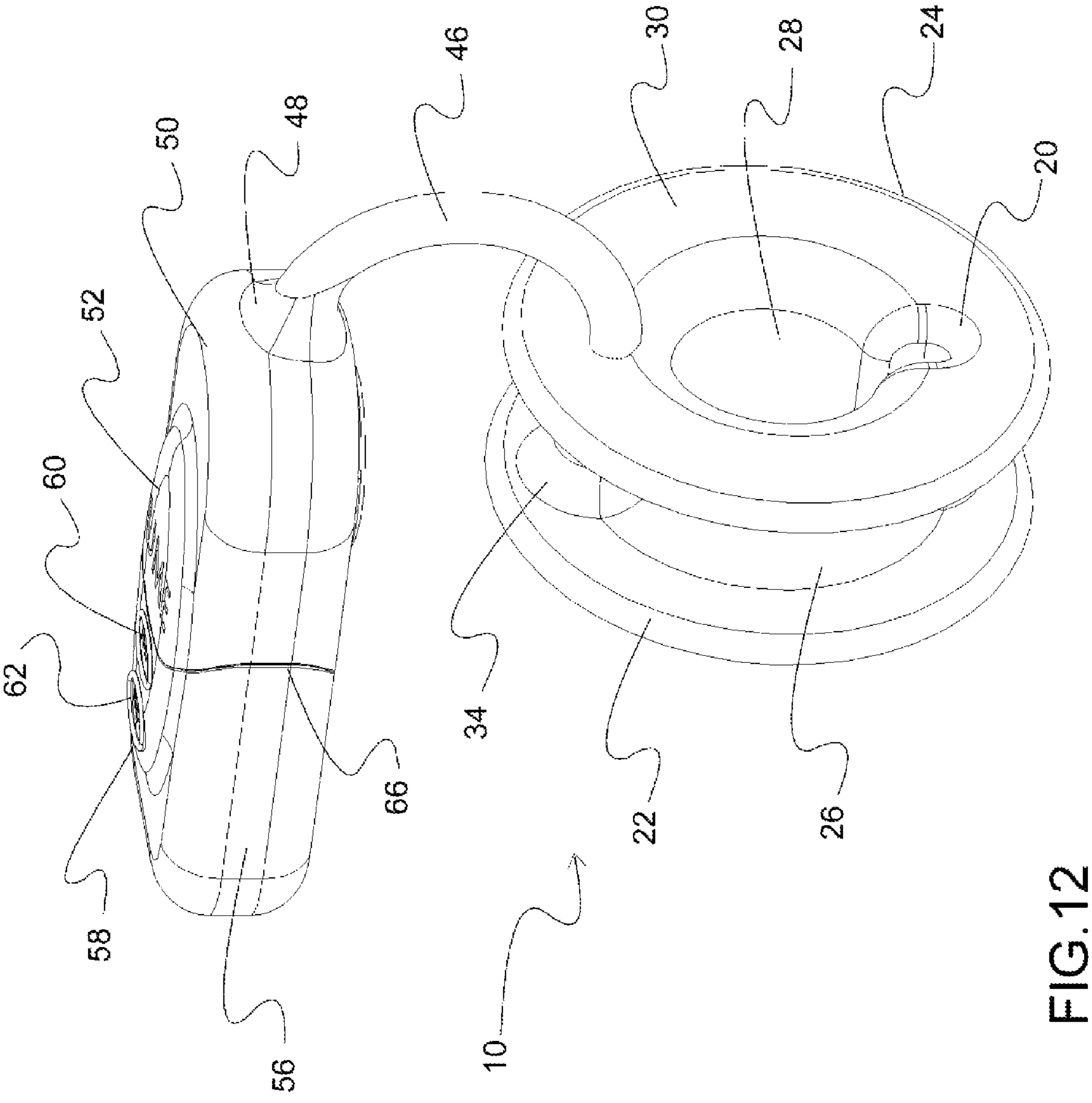
FIG. 12 is a rear perspective view of the device of FIG. 11.

With reference now to FIGS. 11 and 12, a sexual stimulation device 10' according to a second preferred embodiment of the invention is constructed identically as described above, with the exception that the shaft 12 is omitted. In this embodiment, a male inserts his penis through the opening 28 provided through the retaining rings 22 and 24. A condom may also be worn.

Figure 13:
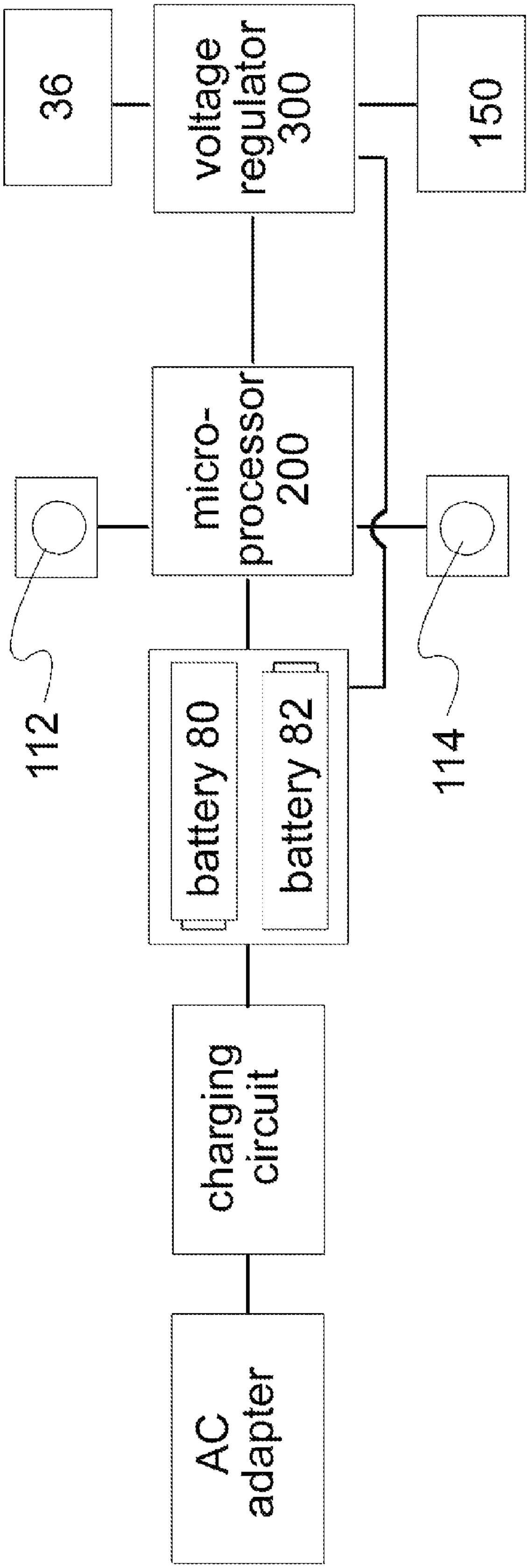
FIG. 13 is a block diagram illustrating electrical components of the sexual stimulation device according to the present invention.

With reference to FIG. 13, the sexual stimulation device according to both the first 10 and second 10' embodiments of the present invention preferably includes a conventional AC adapter to be plugged into an ordinary electrical outlet by a user for recharging purposes. The AC adapter is connected to a charging circuit operative in a conventional manner to charge conventional rechargeable batteries 80 and 82. In use, a user selectively depresses either or both of the three position momentary contact switches 112 and 114 to switch the motors 36 and 150 to high, low, or off speeds. This function is preferably performed by a microprocessor 200 in conjunction with a solid state voltage regulator and power supply circuit 300 operative to provide appropriate voltages to the motors 36 and 150 depending upon the sensed inputs from the switches 112 and 114 to the microprocessor 200.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed is:

1. A sexual stimulation device comprising:

a hollow shaft portion dimensioned to receive a penis and for vaginal insertion;

a vibration producing element connected to said shaft portion;

a housing connected to said shaft by a conduit;

a drive mechanism in said housing for driving said vibration producing element; and a massage element in said housing disposed for providing female stimulation during intercourse.

2. The device of claim 1, wherein said massage element comprises at least one rotating ball.

3. The device of claim 2, further comprising an electric motor operably connected for rotating said at least one ball.

4. The device of claim 1, wherein said massage element comprises a plurality of caged rotating balls rotatably driven by an electric motor.

5. The device of claim 1, wherein said massage element comprises:

a ring gear including a plurality of ball cups;

a plurality of balls received for rotation in said cups; and an electric motor connected for rotating said balls.

6. The device of claim 5 further comprising an elastomeric covering disposed over said balls.

7. The device of claim 1, further comprising at least one annular retaining ring on an end portion of said shaft, said annular retaining ring having an opening communicating with a hollow interior of said shaft and a longitudinally extending channel portion providing sufficient resilience to said retaining ring to provide a resilient friction retaining force to retain said shaft in position during sexual intercourse.

8. The device of claim 1, further comprising a pair of spaced annular retaining rings disposed adjacent an end portion of said shaft, said retaining rings having an opening communicating with a hollow interior of said shaft and a longitudinally extending channel portion providing sufficient resilience to said retaining ring to provide a resilient friction retaining force to retain said shaft in position during sexual intercourse.

9. The device of claim 1, further comprising a plurality of radially enlarged ridges spaced longitudinally along said shaft.

10. A sexual stimulation device comprising:

a hollow shaft portion dimensioned to receive a penis and for vaginal insertion;

a pair of spaced annular retaining rings disposed adjacent an end portion of said shaft, said retaining rings having an opening communicating with a hollow interior of said shaft and a longitudinally extending channel portion providing sufficient resilience to said retaining ring to provide a resilient friction retaining force to retain said shaft in position during sexual intercourse;

a housing connected to said shaft; and a massage element in said housing disposed for providing female stimulation during intercourse.

11. The device of claim 10, wherein said massage element comprises at least one rotating ball.

12. The device of claim 11, further comprising an electric motor operably connected for rotating said at least one ball.

13. The device of claim 11, wherein said massage element comprises a plurality of caged rotating balls rotatably driven by an electric motor.

14. The device of claim 11, wherein said massage element comprises:

a ring gear including a plurality of ball cups;

a plurality of balls received for rotation in said cups; and an electric motor connected for rotating said balls.

15. The device of claim 14 further comprising an elastomeric covering disposed over said balls.

16. A sexual stimulation device comprising:

a hollow shaft portion dimensioned to receive a penis and for vaginal insertion;

a pair of spaced annular retaining rings disposed adjacent an end portion of said shaft, said retaining rings having an opening communicating with a hollow interior of said shaft and a longitudinally extending channel portion providing sufficient resilience to said retaining ring to provide a resilient friction retaining force to retain said shaft in position during sexual intercourse;

a first electric motor disposed in a chamber extending transversely between said annular retaining rings and driving an eccentric flywheel for producing vibration;

a housing connected to said shaft by a conduit;

at least one battery in said housing and connected for driving said first electric motor by a cable extending through said conduit;

a massage element in said housing disposed for providing female stimulation during intercourse, said massage element comprising a ring gear including a plurality of ball cups;

a plurality of balls received for rotation in said cups;

a second electric motor connected for rotating said ring gear; and an elastomeric covering disposed over said balls.

* * * * *